United States Patent
Conant et al.

Patent Number: 6,159,382
Date of Patent: Dec. 12, 2000

[54] WASTE ACID RECOVERY

[75] Inventors: Lawrence D. Conant, West Bridgewater; Arie Keus, Lynn, both of Mass.

[73] Assignee: Waterworks International Inc., Woburn, Mass.

[21] Appl. No.: 09/167,563

[22] Filed: Oct. 7, 1998

Related U.S. Application Data

[63] Continuation-in-part of application No. 08/831,337, Mar. 31, 1997, abandoned.

[51] Int. Cl.[7] .................................................. C01B 17/90
[52] U.S. Cl. .......................... 210/712; 210/702; 210/737; 210/774; 210/787; 62/532; 23/295 R; 423/522; 423/531
[58] Field of Search .............................. 62/532; 423/522, 423/531; 210/702, 712, 737, 774, 787

[56] References Cited

U.S. PATENT DOCUMENTS

| | | |
|---|---|---|
| 2,254,788 | 9/1941 | Ballard . |
| 2,287,732 | 6/1942 | Frey et al. . |
| 2,593,128 | 4/1952 | Felter . |
| 2,662,812 | 12/1953 | Shaw . |
| 2,716,592 | 8/1955 | Skelly et al. . |
| 2,816,822 | 12/1957 | Hess et al. . |
| 2,857,247 | 10/1958 | Putney . |
| 2,862,791 | 12/1958 | Stiles et al. . |
| 3,049,889 | 8/1962 | Carfagno . |
| 3,158,004 | 11/1964 | Klencke ...................................... 62/532 |
| 3,248,890 | 5/1966 | Oman . |
| 3,277,667 | 10/1966 | Hedrick ...................................... 62/343 |
| 3,344,616 | 10/1967 | Owen . |
| 3,400,548 | 9/1968 | Drayer . |
| 3,406,741 | 10/1968 | Leach . |
| 3,410,335 | 11/1968 | Malmstrom et al. . |
| 3,565,168 | 2/1971 | Powell ............................... 165/DIG. 2 |
| 3,607,035 | 9/1971 | Jones . |
| 3,616,268 | 10/1971 | Philbou ...................................... 203/16 |
| 3,689,217 | 9/1972 | Capaul et al. ........................... 423/531 |
| 3,885,399 | 5/1975 | Campbell .................................. 62/123 |
| 3,890,097 | 6/1975 | Minor . |
| 4,091,635 | 5/1978 | Ogman ..................................... 62/123 |
| 4,163,047 | 7/1979 | Dorr . |
| 4,169,054 | 9/1979 | Cappello et al. . |
| 4,314,455 | 2/1982 | Engdahl .................................... 62/124 |
| 4,328,677 | 5/1982 | Meckler .................................... 62/124 |
| 4,394,364 | 7/1983 | Hakl ........................................ 423/483 |
| 4,468,930 | 9/1984 | Johnson ...................................... 62/71 |
| 4,475,355 | 10/1984 | Thijssen .................................... 62/123 |
| 4,551,159 | 11/1985 | Goldstein .................................. 62/541 |
| 4,655,790 | 4/1987 | Wiewiorowski et al. . |
| 4,718,480 | 1/1988 | Kito et al. ................................. 165/94 |
| 4,740,281 | 4/1988 | Chlanda et al. . |
| 4,894,170 | 1/1990 | Billmyre ................................. 210/712 |
| 4,936,114 | 6/1990 | Engdahl et al. ........................... 62/532 |
| 4,954,322 | 9/1990 | DeMarthe ................................. 423/95 |
| 5,102,544 | 4/1992 | Roodenrijs ............................. 210/296 |
| 5,181,396 | 1/1993 | Saari ....................................... 62/541 |

(List continued on next page.)

FOREIGN PATENT DOCUMENTS

| | | |
|---|---|---|
| 52-140497 | 11/1977 | Japan . |
| 150902 | 2/1932 | Switzerland . |
| 796343 | 6/1958 | United Kingdom . |

OTHER PUBLICATIONS

Gable et al. "Phase Equilibria of the System Sulfur Trioxide–Water," *Journal American Chemical Society*, vol. 72, Apr. 1950, pp. 1445–1448.

(List continued on next page.)

*Primary Examiner*—David A. Reifsnyder
*Attorney, Agent, or Firm*—Morgan, Lewis & Bockius LLP

[57] ABSTRACT

A process for purifying a sulfuric acid solution such as by cooling a sulfuric acid solution to at or near its freezing point to form a slurry of a solid phase and a liquid phase. The slurry has an acid-rich region and an acid-poor region. The acid-rich region is separated from the acid-poor region on the basis of density.

15 Claims, 8 Drawing Sheets

U.S. PATENT DOCUMENTS

| | | | |
|---|---|---|---|
| 5,220,802 | 6/1993 | Kiczek et al. | 62/374 |
| 5,228,885 | 7/1993 | Wagner et al. . | |
| 5,275,701 | 1/1994 | Mazzafro et al. | 203/12 |
| 5,388,414 | 2/1995 | Cheng . | |
| 5,394,706 | 3/1995 | Keus | 62/123 |
| 5,537,832 | 7/1996 | Keus | 62/544 |
| 5,575,160 | 11/1996 | Keus | 62/544 |

OTHER PUBLICATIONS

T.R. Rubin and W.F. Giauque, "The Heat Capacities and Entropies of Sulfuric Acid and Its Mono–and Dihydrates From 15 to 300°K.[1]," *Journal American Chemical Society*, vol. 74, Feb. 5, 1952, pp. 800–803.

T.R. Bump and Wilmer L. Sibbitt, "Aqueous Solutions of Nitric Acid and of Sulfuric Acid," *Industrial and Engineering Chemistry*, vol. 47, No. 8, Aug. 1955, pp. 1665–1670.

Refrigeration Resources, "Chill Steel–Pickling Acids to Ease Metals Recovery," *Chemical Engineering*, Nov. 1995, p. 186C.

F. J. Zeleznik, "Thermodynamic Properties of the Aqueous Sulfuric Acid System to 350 K," *Journal Physical and Chemical Reference Data*, vol. 20, No. 6, Nov./Dec. 1991, pp. 1157–1200.

Giauque et al., "The Thermodynamic Properties of Aqueous Sulfuric Acid Solutions and Hydrates From 15 to 300°K," *Journal American Chemical Society*, vol. 82, Jan. 5, 1960, pp. 62–70.

Kunzler et al., "The Freezing Point Curves of Concentrated Aqueous Sulfuric Acid," *Journal American Chemical Society*, vol. 74, No. 21, Nov. 1952, pp. 5271–74.

Hornung et al., "The Heat Capacities and Entropies of Sulfuric Acid Tri—and Tetrahydrates," *Journal American Chemical Society*, vol. 77, Jun. 1955, pp. 2983–87.

Hornung et al., "The Low Temperature Heat Capacity and Entropy of Sulfuric Acid Hemihexahydrate. Some Observations on Sulfuric Acid "Octahydrate","*Journal American Chemical Society*, vol. 78, Nov. 1956, pp. 5747–51.

Jaecker–Voirol et al., "Vapor Pressures in the Ternary System Water–Nitric Acid–Sulfuric Acid at Low Temperatures," Journal of Geophysical Research, vol. 95, No. D8, Jul. 1990, pp. 11, 857–63.

Worsnop et al., "Vapor Pressures of Solid Hydrates of Nitric Acid: Implications for Polar Stratospheric Clouds," *Science*, vol. 259, Jan. 1993, pp. 71–74.

Zhang et al., "Vapor Pressure Measurements for the $H_2SO_4/HNO_3/H_2O$ and $H_2SO_4/HCl/H_2O$ Systems: Incorporation of Stratospheric Acids into Background Sulfate Aerosols," *Journal of Physical Chemistry*, vol. 97, No. 32, Aug. 12, 1993, pp. 8541–48.

WASTE ACID RECOVERY

CONTINUING DATA

This application is a continuation-in-part of application Ser. No. 08/831,337, filed Mar. 31, 1997 now abandoned, the disclosure of which is incorporated by reference herein.

FIELD OF THE INVENTION

The invention relates generally to a process for purifying a sulfuric acid solution, and more particularly, to a freeze concentration method of purifying an aqueous sulfuric acid solution by cooling the aqueous sulfuric acid solution to a temperature at or near its freezing point and separating the resulting acid-rich region from the acid-poor region.

BACKGROUND OF THE INVENTION

The treatment and disposal of spent industrial process waste waters, particularly acid-containing waste waters, has been a long standing problem in many industries. Acid-containing waste waters, also known as spent acid streams, are by-products of numerous manufacturing and refining processes. Increasingly higher disposal costs and numerous environmental issues connected with "hazardous" waste disposal have accentuated the need to treat acid-containing waste waters. For example, many local municipalities are enacting measures designed to encourage industrial waste water generators to seek alternative methods of treatment that do not rely on traditional neutralization and landfill practices. The pressure for new treatment methods is also enhanced by the diminishing amounts of landfill space capable of handling spent industrial waste water, and acid-containing waste water in particular.

Sulfuric acid is, by far, one of the most widely used chemicals in industrial chemistry. Annually, sulfuric acid production in the United States exceeds 48 million tons. Sulfuric acid is used, for example, in etching processes, in electroplating processes, in battery acids, in fertilizers, in catalysts such as hydrocarbon refining alkylation, as well as a reagent for chemical synthesis. From such uses, one-third, or up to 16 million tons per year of sulfuric acid must be disposed of as an acid-containing waste. Current disposal methods are inadequate to meet this need, involve costly technologies, and/or generates additional waste to be disposed.

An example of a particular industry in need of recovering sulfuric acid from a waste product is the petroleum industry. Worldwide economic development has resulted in increasing demand for petroleum energy products, especially high-octane gasoline. A class of petroleum-derived compounds known to have particularly high octane ratings are branched paraffins, having from about 6 to 12 carbon atoms. Unfortunately, the amount of naturally occurring $C_{6\text{-}12}$ paraffins in crude petroleum is limited and is insufficient to meet the increasing demand for high octane blends. Accordingly the petroleum industry has relied upon sulfuric acid catalysts to aid in synthesizing branched paraffins from existing materials to supplement the naturally existing supply of such high-octane materials. The sulfuric acid catalysts aid in the alkylation of short-chain isoparaffins with short-chain olefins, derived from various refinery processes. A more detailed discussion of sulfuric acid alkylation is provided in L. F. Albright et al., "Alkylation of Isobutane with $C_4$ Olefins," 27 Ind. Eng. Chem. Res., 381–397, (1988), herein incorporated by reference in its entirety. Unfortunately, as described by L. F. Albright et al., a large volume of sulfuric acid catalyst is necessary to catalyze the alkylation process as the sulfuric acid employed should be fresh or relatively pure sulfuric acid. Consequently, the hydrocarbon alkylation process produces large quantities of a waste product containing sulfuric acid for which the disposal costs continue to rise.

Neutralization is the most popular method of waste sulfuric acid solutions. To neutralize sulfuric acid, a variety of bases are added to a sulfuric acid wastewater stream until the stream has been totally neutralized. A considerable drawback to this process is that for every ton of acid, four tons of base are generally required. Thus, for every ton of sulfuric acid, neutralization disposal techniques produce five tons of waste generally requiring landfill disposal.

Reverse osmosis has also been used to treat or dispose of sulfuric acid. Reverse osmosis forces waste sulfuric acid through costly filtration systems until the acid content of the stream is reduced to a level where the remaining stream can be disposed of by conventional means. This requires an expensive filtration system which is generally difficult to build and maintain. Moreover, current reverse osmosis filtration systems are only effective for treating small volume streams.

Evaporation represents another possible disposal method to treat sulfuric acid-containing wastes. However, to dissipate or remove water from an aqueous sulfuric acid solution requires significant energy input and, therefore, carries a high cost.

Incineration may be also used to dispose of waste sulfuric acid. Like evaporation, incineration is not expensive but may lead to the creation of acid rain. The possibility of acid rain makes incineration environmentally unacceptable.

As a result of the limitations in current disposal methods, there exists a need for a cost effective and environmentally prudent method to treat and/or dispose of waste sulfuric acid. A further need exists to reduce the amount of sulfuric acid-containing waste requiring ultimate disposal in a landfill. A preferable answer to this need would be to recycle spent sulfuric acid streams such that they may be reused. Recycling sulfuric acid would also answer and reduce the need for landfill disposal. While many sulfuric acid recycling processes have been proposed in the past (see, e.g., U.S. Pat. Nos. 4,163,047, 4,954,322, 5,275,701 and 5,228,885) to date, there has been no commercially feasible process to recycle spent sulfuric acid streams.

SUMMARY OF THE INVENTION

The invention answers the problems arising from sulfuric acid disposal by providing a cost effective and environmentally prudent method of purifying an aqueous industrial sulfuric acid solution to produce a reusable acid product. The method of the invention is particularly useful with aqueous solutions of sulfuric acid which are employed in industrial processes or are formed as by-products or waste streams of industrial processes, such as in hydrocarbon alkylation refining processes. By purifying an aqueous sulfuric acid solution, the invention recycles sulfuric acid for consumption and reduces the amount of sulfuric acid waste requiring disposal.

More specifically, the invention provides a method of purifying, or enriching, an aqueous sulfuric acid solution through the use of a freeze crystallization process in which an aqueous sulfuric acid solution is cooled to a temperature at or near its freezing point to form a slurry of a solid phase and a liquid phase. This cooled slurry mixture contains an acid-rich region and an acid-poor region which are subsequently separated on the basis of density. The sulfuric acid concentration in the aqueous sulfuric acid solution typically ranges from 10–95% by weight. The aqueous sulfuric acid solutions may also contain acids other than sulfuric acid, such as nitric and hydrochloric acid. By purifying the aqueous sulfuric acid solution, impurities contained in the solution may be removed and the concentration of the sulfuric acid may be increased, to levels sufficient for recycling and reuse.

Various processes and apparatus for carrying out the purification process are contemplated but the freeze concentration apparatus disclosed in the assignee's U.S. Pat. No. 5,394,706 is preferred. The cooling of the aqueous sulfuric acid solution may occur in a conventional heat exchanger. One embodiment of the invention separates the acid-rich region from the acid-poor region on the basis of density in a density column. In another embodiment of the invention, the separation occurs by centrifuging the cooled slurry to separate the acid-rich region from the acid-poor region. In a further embodiment, the separation step involves sequentially feeding the solid-liquid phase slurry through a combination of a density column and a centrifuge and separating the acid-rich region from the acid-poor region on the basis of density. Another embodiment of the invention employs the cooled, separated, acid-rich region and/or acid-poor region to precool an aqueous sulfuric acid solution entering the method to be purified. The method of the invention may be a continuous or batch process. In a continuous process, a portion of the separated acid-rich region or the separated acid-poor region may be mixed with the initial aqueous sulfuric acid solution in order to control the sulfuric acid concentration of the solution to be purified.

Other advantages and features of the invention will be apparent from consideration of the detailed description of the invention provided below.

DETAILED DESCRIPTION OF THE PREFERRED EMBODIMENTS

The invention provides a commercially feasible method of purifying an aqueous sulfuric acid solution on a large commercial scale. The method may be used with any sulfuric acid solution, such as those mentioned above, having impurities but is particularly useful for aqueous sulfuric acid solutions resulting from industrial processes, such as hydrocarbon refining involving alkylation. Such solutions contain not only sulfuric acid but other by-products from the particular process, such as organic impurities or waste products. The method of the invention may remove the impurities, purify the aqueous sulfuric acid, and permit its reuse in the same or a different process. To purify an aqueous sulfuric acid solution, the method cools an aqueous sulfuric acid solution to at or near its freezing point to form a slurry of a solid phase and a liquid phase. The cooled mixture contains an acid-rich region and an acid-poor region. The method separates the acid-rich region from the acid-poor region on the basis of their different densities.

The invention takes advantage of the relationship between the solid and liquid phases of a mixture of two components—sulfuric acid dissolved in water. When a solute, such as sulfuric acid, is dissolved in another substance, such as water, the temperature at which the liquid composition becomes a solid depends, not only upon temperature, but also upon the concentration of the system. This relationship may be depicted using a phase diagram such as in FIG. 1, which shows a typical phase diagram for a mixture of a binary solution of compounds A and B. The phase diagram consists of a horizontal axis of weight percent of one component and a vertical axis of temperature. The normal shape of the relationship of the solid and liquid phases is depicted by a curve that shows decreasing temperature with increasing concentration to a point called the "eutectic point." At concentrations higher than the eutectic point, the curve rises in temperature with increasing concentration. This curve is called the "saturation curve." In other words, the curve represents the highest concentration of A for a saturated solution at a given temperature. A change in temperature, for example pushing below the saturation curve, results in a change in concentration.

Figure 1:
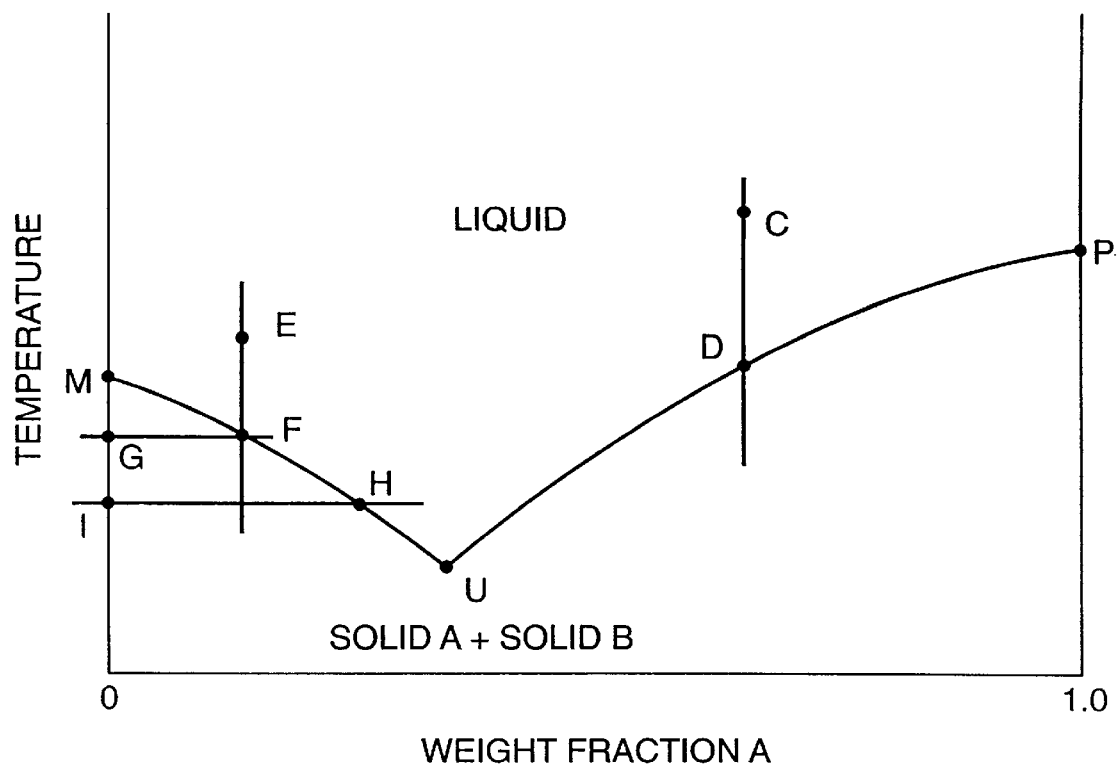
FIG. 1 is a sample of phase diagram for a binary mixture.

In the solid-liquid phase diagram of FIG. 1, M is the melting point of pure B and P is the melting point of pure A. The curves MFHU and PDU represent the solubilities of components B and A, respectively, in their liquid solution. For example, a liquid solution at point E, if cooled, precipitates B, so the solution becomes richer in A. At point G, the liquid and solid A are in equilibrium at a temperature corresponding to points F and G. As the temperature is lowered below point F, additional B precipitates (represented as point I), while the concentration or weight fraction of component A in the liquid composition gradually increases, which is represented on the diagram by moving along the curve FHU through point H and toward U. The point U represents the eutectic point for the mixture of A and B. If the temperature is further lowered to a point corresponding to U, the liquid remaining is a eutectic mixture, and any further cooling results in complete solidification of a mixture of A and B without a change in concentration. This solid is called the eutectic solid. Similarly, if the liquid solution was originally at C and cooled to D, the solid precipitating would be A. Further cooling at this condition will result in pure A until the eutectic point U is reached.

As shown by the phase diagram in FIG. 1, a saturated solution, when cooled, preferentially precipitates one component, the solute, as the solution changes in concentration toward the eutectic point. In general, the component precipitates in its pure form as crystals. As they form, the crystals exclude other impurities present in the original solution. Collecting the crystals, then, provides a means for obtaining a purified product. Freeze concentration systems and methods like the invention operate by taking advantage of this principle.

In the case of a simple binary system, the solid phase, in theory, does not contain any solvent when the composition of liquid which is partially frozen is on either side of the eutectic composition. In practice, it is very difficult to attain this condition, and often the solid phase A does contain B because of volumetric inclusions. Also, there may be slight solid solubility in the ultrapure region.

Figure 2:
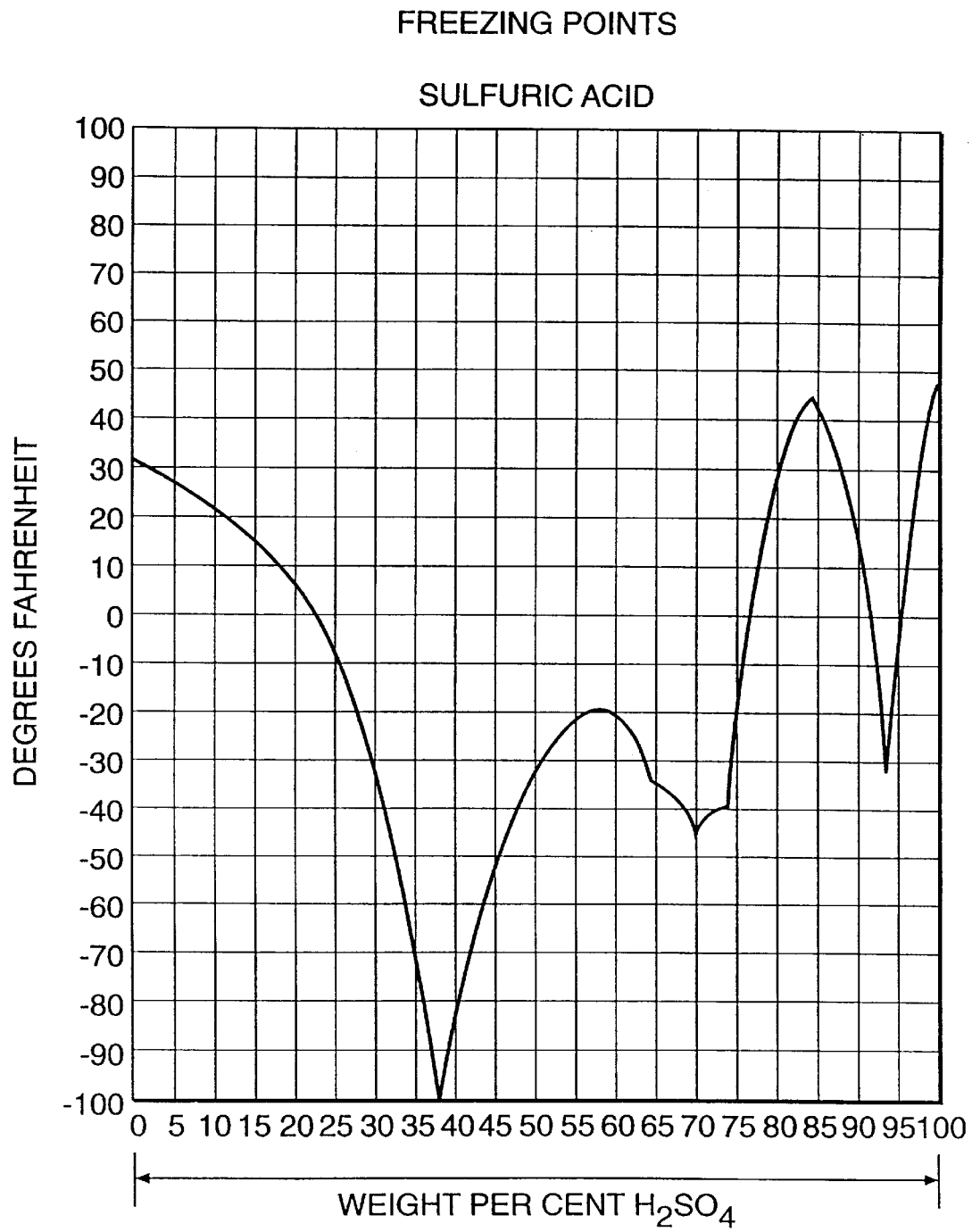
FIG. 2 is a phase diagram for sulfuric acid in water. Taken from Gable, Eetz & Maron, JACS, vol. 72, 1446–1448 (1960).

As shown by the solid-liquid phase diagram in FIG. 2, an aqueous solution of sulfuric acid differs significantly from a simple binary system, such as shown in FIG. 1. Sulfuric acid is the nonvolatile product of the reaction of sulfur trioxide ($SO_3$) and water ($H_2O$). By convention, mixtures of sulfur trioxide and water are expressed as percent sulfuric acid. An aqueous solution of sulfuric acid forms several eutectic points and displays a complicated phase diagram. This is due at least in part to the ability of sulfuric acid to form hydrates with water. For example, sulfuric acid with water can form a monohydrate, $H_2SO_4 \cdot H_2O$, a dihydrate, $H_2SO_4 \cdot 2H_2O$, a trihydrate, $H_2SO_4 \cdot 3H_2O$ and a tetrahydrate, $H_2SO_4 \cdot 4H_2O$. The freezing point for sulfuric acid concentrations between 0% and 38% by weight varies from 32° F. to −100° F. For sulfuric acid concentrations varying between about 38% to 74% by weight the freezing point is less than −20° F. Interestingly, the freezing point for sulfuric acid concentrations ranging from about 74% to 94% by weight varies from a low of about −32° F. to a high of about 48° F. The sulfuric acid concentration region of from about 94% to 100% by weight has a freezing point temperature range of from about −32° F. to about 50° F.

The method of this invention applies principles such as those just discussed to purify an aqueous solution of sulfuric acid. The method cools an aqueous sulfuric acid solution to at or near its freezing point to create a solid-liquid slurry having an acid-rich region and an acid-poor region. The acid-rich region and acid-poor region may then be separated on the basis of density. The acid-rich region generally possesses a higher density than the acid-poor region.

The inventive method of purifying aqueous sulfuric acid may be used with any aqueous sulfuric acid solution. Of particular interest are aqueous sulfuric acid concentrations ranging from about 10–95% by weight, preferably about 20–95% by weight and most preferably about 74–95% by weight. The solution may contain other acids, such as nitric acid or hydrochloric acid, in combination with the sulfuric acid solution. Such mixed acid solutions are often used in industrial processes or formed as a by-product. When other acids are present in combination with sulfuric acid, the combined total acid concentration generally will range from about 10–50% by weight, more preferably about 10–40% by weight and most preferably 10–30% by weight.

The aqueous sulfuric acid solution may contain impurities resulting from the process giving rise to the solution itself. Impurities for the purpose of the invention are defined as compounds other than water, sulfuric acid or hydrates of sulfuric acid, or other acids if the sulfuric acid solution is a mixed acid solution. Typical impurities include organics, organometallics and metals, including the salts and oxides of metals. Possible organic impurities include, for example, reaction by-products; volatile organic compounds, (VOC's); oils and other hydrocarbons, including petroleum compounds; surfactants; resins; and plastic residues. Typical metal impurities include sodium, lithium and heavy metals such as iron, copper, lead, chromium. By practicing the method of the invention, such impurities contained in the aqueous solution may be removed and the aqueous sulfuric acid purified. Because the method of the invention separates an acid-rich region from an acid-poor region, the method advantageously may also increase the concentration of the sulfuric acid in the aqueous sulfuric acid solution product. Using the method of the invention, the sulfuric acid concentration may be increased, or enriched, by recovering the acid-rich region, for example up to 15%. Typical methods of the invention enrich the sulfuric acid concentration in an amount of from 0.01–10%.

An example of a preferred aqueous sulfuric acid solution which may be purified by the method of the invention is an aqueous waste stream containing sulfuric acid and organic impurities, such as that resulting from a petroleum hydrocarbon refining or alkylation processes. Generally, the aqueous waste stream contains from about 74–90% by weight sulfuric acid, 6–16% by weight organic impurity and about 4–10% by weight water. In a preferred embodiment the aqueous waste stream is a waste recovered from a sulfuric acid catalyzed, hydrocarbon alkylation process wherein the organic waste contains a mixture of hydrocarbons and other VOC's. Generally, the freezing point for an organic waste product containing about 74 to about 90 wt % sulfuric acid will vary from about 10 to 50° F.

Accordingly, a preferred method of the invention involves recovering a sulfuric acid from an aqueous waste stream containing sulfuric acid and an organic impurity. This method comprising the steps of: cooling the aqueous waste stream to a temperature at or near its freezing point to form a slurry of a solid sulfuric acid-rich phase and a liquid phase containing the organic impurity; and separating the sulfuric solid acid-rich phase and the liquid organic impurity phase on the basis of density. The separated solid sulfuric acid phase may then be warmed to a temperature (e.g., ambient temperature) to give a purified sulfuric acid solution.

The method of the invention will now be described by referring to an aqueous sulfuric acid purification system of the invention as shown in schematic form in FIG. 3. Ancillary equipment, such as pumps, valves and the like, which may be necessary for operation of the system but which are not needed to explain the principles of the invention have not been shown nor described for purposes of clarity. It will be recognized by those skilled in the art that such ancillary equipment would, of course, be used in combination with the method and apparatus to practice the invention.

In the invention, the aqueous sulfuric acid solution is cooled to a temperature at or near its freezing point to form a solid-liquid slurry. The cooling step requires that the aqueous sulfuric acid be delivered, for example by means of a conduit 10, to an appropriate heat exchanger 14. The sulfuric acid solution is preferably free of solids prior to entering the heat exchanger 14. Inside the heat exchanger 14 the sulfuric acid solution is cooled such that a portion of the sulfuric acid solution forms a solid phase. In order to form such a solid phase, the sulfuric acid solution is cooled to at or near its freezing point. However, care must be taken such that only a portion of the aqueous sulfuric acid solution is cooled to form a solid crystalline material, hereinafter referred to as the solid phase. As mentioned above, upon formation the solid phase will exclude dissolved organic and inorganic impurities.

The solid phase formed in the heat exchanger 14 remains in contact with the liquid phase such that a solid-liquid slurry is formed having an acid-rich region and an acid-poor region. An acid-rich region is defined as a portion of the solid-liquid slurry that will separate on the basis of density to form a region having a higher sulfuric acid content than the remaining solid-liquid slurry. Depending on the sulfuric acid concentration of the initial aqueous sulfuric acid solution, the acid-rich region may be either the solid phase or liquid phase. Likewise, depending on the initial sulfuric acid concentration, the acid-poor region may be either the solid or liquid phase. Typically, the solid phase will contain sulfuric acid alone or in a hydrated form and will be the acid-rich region. The acid-rich region is also the higher density portion of the slurry.

A particularly preferred heat exchanger 14 for use in the invention is a scraped-surface freeze crystallizer described by the assignee's U.S. Pat. No. 5,394,706, the disclosure of which is incorporated by reference herein. The scraped-surface crystallizer of this patent produces, removes, and pumps ice crystals in an economical and energy efficient manner. The main body of the crystallizer is made from an outer shell, a tube sheet on the feed or product inlet side, a tube sheet on the slurry discharge side, and a plurality of tubes disposed inside the shell and having ends supported by the tube sheets. The inner surface of the plurality of tubes are polished to facilitate ice scrapping and slurry flow. Positioned axially within each tube is a rod which is connected to a shaft at one end and a scrapper at the other. The scrapper is designed such that the flow of ice crystals through the tube is not impeded. The shaft is connected to a conventional drive motor, piston or other mechanism that imparts a back-and-forth or reciprocal motion to the shaft, rod and scrapper.

However, any heat exchanger capable of cooling a feed stream to at or near its freeze point may be used in a method of the invention. The heat exchanger, is supplied with a suitable refrigerant at a temperature and flow rate such that a portion of the aqueous sulfuric acid freezes to form a solid phase. While the desired temperature of the refrigerant will depend upon the nature and concentration of the aqueous sulfuric acid stream, generally the refrigerant temperature will be about −40° F. or higher, preferably about −30° F. or higher.

Any conventional refrigeration means 15 may be used to cool the heat exchanger. One such refrigeration means for the heat exchanger is a brine solution passed between a series of bundled tubes disposed within the shell of the heat exchanger as disclosed in U.S. Pat. No. 5,394,706. However, no matter which particular type of heat exchanger and refrigerant is used, the temperature conditions in the heat exchanger depend upon the concentration of the aqueous sulfuric acid stream and its corresponding freezing point. For example, the freezing point for an aqueous waste stream containing an organic impurity containing about 74 to about 90 wt % sulfuric acid will vary from about 10 to 50° F.

In order to properly control the crystallization process, the heat exchanger 14 will preferably contain devices capable of monitoring and controlling the cooling process. Thus, the heat exchanger may contain a differential temperature gauge across the crystallizer, and a pressure measuring device. By properly monitoring the cooling process, the refrigerant flowing through the heat exchanger can be varied to prevent the contents of the crystallizer from completely solidifying. Should the sulfuric acid feed stream completely solidify the heat exchanger should be shut down and thawed.

Another method of cooling the aqueous sulfuric acid solution is by direct injection of one or more refrigerants into the solution. However, this method of cooling is not preferred as it requires the refrigerant to be removed at a later stage, for example by evaporation. Cooling the solution to its triple point in a multistage flash evaporator may also be used. However, working at the triple point is not generally preferred due to the inherent difficulties in maintaining the solution at its triple point.

When the heat exchanger 14 is the preferred scraped-surface crystallizer, the aqueous sulfuric acid solution is conducted through the tubes where it is cooled and a solid phase forms on the interior of the tubes. The motion of the scraper causes the solid phase to be removed or scraped from the tube surface mixing with the liquid phase to form a solid-liquid slurry. The solid-liquid slurry, formed in the crystallizer, contains an acid-rich region and an acid-poor region. This slurry is pumped out from the crystallizer and into a separator 16 via conduit line 11.

In the separator 16, the acid-rich region and acid-poor regions are separated on the basis of their differing density with the acid-rich region generally having the greater density. Generally, both the acid-rich region and the acid-poor region will both contain some solid and liquid phase material. Typically, for higher initial sulfuric acid concentrations, the sulfuric acid-rich region will have a larger amount of the denser solid phase and the sulfuric acid-poor region a larger amount of the lighter liquid phase. If the slurry contains a large amount of the solid phase, a portion of the solid phase may be melted to wash the remaining solid phase, to improve flow, or to free trapped or entrained impurities.

Separating the acid-rich region from the acid-poor region may be accomplished with any conventional density separation apparatus. Preferably, the separation occurs in a density column, a centrifuge, or in a sequential combination of the two.

When the separator 16 is a dynamic density column, the aqueous sulfuric acid solid-liquid slurry, containing an acid-rich region and an acid-poor region is generally conducted via line 11 to the mid-section of the density column. For a static density column the slurry is generally conducted to the top of the density column. A density column is a gradient device, with higher density materials settling toward the bottom of the device and lower density materials rising to the top. The density column may be of any conventional design known in the art. A preferred dynamic density column is the wash column described in U.S. Pat. No. 5,394,706. A preferred density column contains pin mixing rods allowing easier separation of the solid-liquid slurry into at least one acid-rich region and at least one acid-poor region. If a density column having pin mixing rods is utilized, the rate of rotation of the pin mixing rods must be known and controlled.

Figure 3:
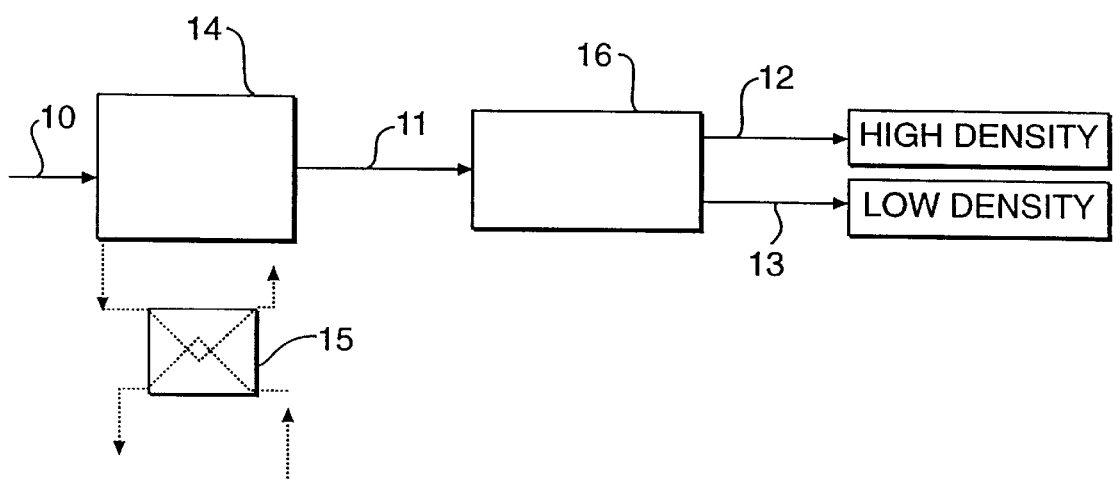
FIG. 3 is a schematic flow diagram illustrating a freeze concentration process of the invention.

Referring to FIG. 3 and density column (separator 16), the aqueous sulfuric acid solid-liquid slurry enters the density column and remains for a time sufficient to allow separation on the basis of density. Depending upon the initial concentration of the aqueous sulfuric acid solution, the higher density material may be either the acid-rich region or the acid-poor region. The higher density portion of the slurry is be removed as "bottoms" from the density column through line 12 and lower density portion as "overheads" through line 13. The time spent in the density column is known as the "residence time." Given enough time the various concentrations of the acid-rich region and acid-poor region will return to the initial liquid aqueous sulfuric acid solution. Additionally, some of the frozen solid phase may be returned to a liquid phase due to the heat generated by mixing the various concentrations of sulfuric acid. This may increase the possibility of returning to the initial homogeneous concentration. However, the poor heat transfer characteristics inherent in a solid-liquid slurry works against this liquefication. If the heat of mixing is deemed unacceptably high, which may occur in large density columns, cooling jackets may be used to remove excess heat. Thus, the residence time should be long enough to allow separation based on density but not so long as to permit the slurry to revert back to the initial liquid aqueous sulfuric acid solution. While the residence time is generally dependent upon the size and type of density column used, residence times will generally range from about 1 to 60 minutes, preferably about 2 to 30 minutes and most preferably 2 to 10 minutes.

The rate of separation and residence time in the density column will depend upon the relative upward and downward velocities of the acid-rich region and acid-poor region. The rate of downward velocity is increased by the removal rate of the higher density material from the bottom of the column and is decreased by an increased rate of slurry fed into the column.

Specific gravity may be measured to insure that proper separation is achieved. Specific gravity may be monitored manually on a periodic basis.

The temperature of the top and bottom discharge streams should be monitored to insure sufficient separation. Warmer temperatures favor a return to the initial homogenous aqueous sulfuric acid solution as opposed to maintaining separate acid-rich and acid-poor regions.

Another method separating the acid-rich region from the acid-poor region involves the use of a centrifuge as the separator 16. A preferred centrifuge is the rotatable drum separator described in U.S. Pat. No. 5,394,706, which separates a high density material from a low density material by means of two or more drums rotating at different speeds. The first rotatable drum is connected to one end of a hollow drive shaft and may have an approximate length to diameter ratio of 1:1. A second drum is mounted adjacent to the rotatable drum on the opposite side of the hollow drive shaft. The second drum may have a length-to-diameter ratio of approximately 1:10. The insider diameter of the two drums should be equal. The interiors of the drums are separated by a wall which extends radially inward from the second drum. The wall is perforated by a series of small holes in its outer periphery that allow a higher density phase to flow from the interior of the rotatable drum into the interior of the second drum. The wall has a central opening which may have a diameter equal to about one-half of the diameter of the rotatable drum. An auger is located inside the rotatable drum. When the rotatable drum is rotated, the auger is designed to rotate at a different speed, thereby providing for a scrapping motion by the auger. While the residence time in the centrifuge is highly dependent upon the size and type of centrifuge used, residence times will generally range from about 1 to 60 minutes, preferably about 2 to 30 minutes and most preferably 2 to 10 minutes.

When this type of separation apparatus is used, the aqueous sulfuric acid solid-liquid slurry is conducted via line 11 into the rotatable drum of the separator 16. Once inside the rotatable drum the rotation of the rotatable drum and auger causes a centrifugal effect to be produced. Due to the density differences between the acid-poor region and acid-rich regions of the slurry, the higher density material will be conducted through the small holes into the second drum. Depending upon the sulfuric acid concentration of the initial aqueous sulfuric acid solution, the higher density material may be either the acid-rich region or the acid-poor region. A stationary tube located in the second drum allows the higher density material to be conducted out of the second drum. The higher density material is pumped through the stationary tube and into line 12. The motion of the auger in the rotatable drum removes the lower density material and any remaining higher density material from the rotatable drum exiting the centrifuge via line 13.

As discussed above, the acid-rich region may be separated from the acid-poor region using a density column or a centrifuge. Another embodiment of the invention uses a sequential combination of the two in either order. Combining a centrifuge with a density column achieves a higher degree of sulfuric acid purification. When employing both a centrifuge and a density column, the aqueous sulfuric acid solid-liquid slurry exits the heat exchanger to first enter the density column to separate and remove at least a portion of the acid-rich region. The remaining slurry may then be conducted to the centrifuge for further separation. It is also possible to purify the aqueous sulfuric acid by a first separation in the centrifuge followed by a subsequent separation in the density column. Through the use of a density column or centrifuge or both, separation can occur without the need of additional screening or filtration steps used in conventional processes.

Depending upon the nature of the aqueous sulfuric acid solution, it may be desirable to precool the aqueous sulfuric acid solution to a temperature above its freezing point. A cool stream (e.g., the acid-rich or acid-poor region removed from the density column or centrifuge) may be used as the refrigerant to precool the aqueous sulfuric acid solution prior to conducting the solution to the heat exchanger. A precooling heat exchanger may be used to precool the incoming aqueous sulfuric acid solution before the solution enters the heat exchanger to be cooled to form the solid and liquid phase. When the incoming aqueous sulfuric acid solution is precooled, it is possible for some contaminants to precipitate as solids which may be removed by nanofiltration, carbon absorption, ion exchange or other techniques known in the art. Due to the corrosive nature of concentrated sulfuric acid streams, the stream may be diluted with water before precooling and removing any contaminant. Once the contaminant is removed to an acceptable level, the aqueous sulfuric acid may be reconcentrated using the method of the invention.

Preferred embodiments of the inventions, such as a freeze concentration method employing a density column and/or a centrifuge are depicted in FIGS. 4–8. As with FIG. 3, ancillary equipment, such as pumps, valves and the like, however, which may be necessary for operation of the system but which are not needed to explain the principles of the invention have not been shown in FIGS. 4 through 8 nor described for purposes of clarity. It will be recognized by those skilled in the art that such ancillary equipment would, of course, be used in combination with the method and apparatus to practice the invention. Additionally, while some valves, pumps and gauges are depicted in FIGS. 4 through 8, it will be recognized by those skilled in the art that the placement of these devices or their equivalents may be arranged as desired.

Figure 4:
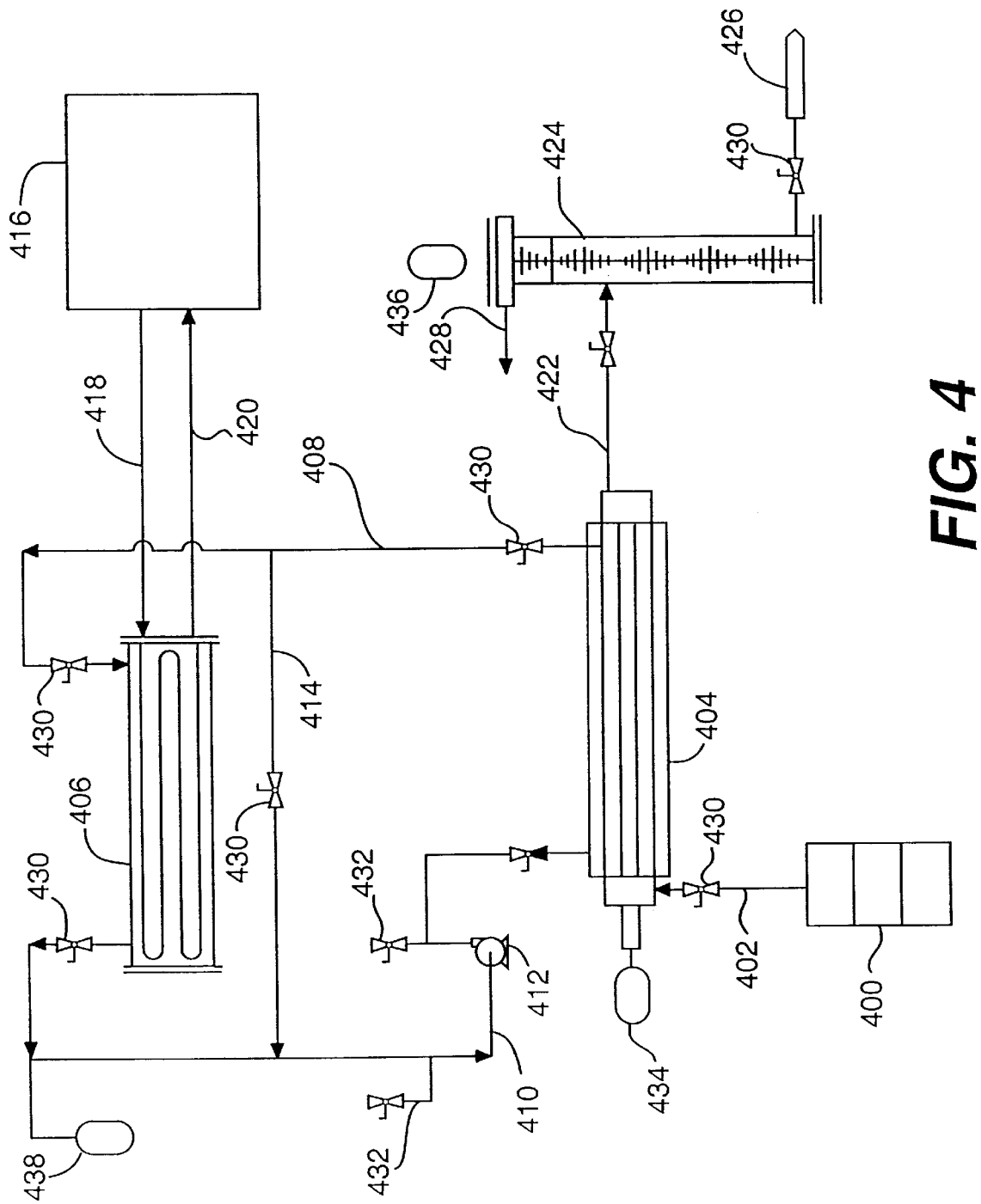
FIG. 4 is a schematic diagram illustrating a typical freeze concentration method of the invention employing a density column.

A typical freeze concentration method of the invention employing a density column is shown in detail in FIG. 4. An initial feed stream 402 is conducted from a feed source 400 to a crystallizer 404. The initial feed stream 402 is cooled in the crystallizer to at or near the freezing point of the feed stream such that a slurry of a solid phase and a liquid phase are formed. In a preferred embodiment, the initial feed stream 402 is cooled and a slurry is formed and pumped out of crystallizer 400 by means of a pumping mechanism 434 and sent via stream 422 to a density column 424.

The crystallizer 404 may be cooled by any conventional and well known refrigeration means such as pumping a refrigerant from a heat exchanger 406 through the crystallizer 404. A conventional refrigeration means for the crystallizer 404 may entail pumping a cooled refrigerant stream 410 via a pump 412 from the heat exchanger 406 into the crystallizer 404 wherein the refrigerant becomes heated. After cooling the crystallizer, the warmed refrigerant 408 may exit the crystallizer 404 and be cooled in the heat exchanger 406. As part of the circulation of the warmed and cooled refrigerant, a recycle stream 414 as well as various pressure gauges 432 and expansion tanks 438 may be employed. Additionally, the heat exchanger 406 may be connected to a conventional refrigeration unit 416 which delivers cooled coolant 418 to the heat exchanger 406, and cools the warmed coolant 420 from heat exchanger 406.

The density column 424 receives the slurry coming from the crystallizer 404 via stream 422. In the density column the slurry is allowed to separate on the basis of density. Typically, the solid phase is of higher density than the liquid phase and will exit the lower portion of the density column via stream 426. The liquid phase will typically have a lower density and will exit the density column via stream 428. To aid in the separation of the solid and liquid phases, a mixer 436 may be employed in the density column 424. Of course it is understood that in the freeze concentration method various valves or solenoids 430 or their equivalents may be used to control or regulate the flow of the process streams.

Figure 5:
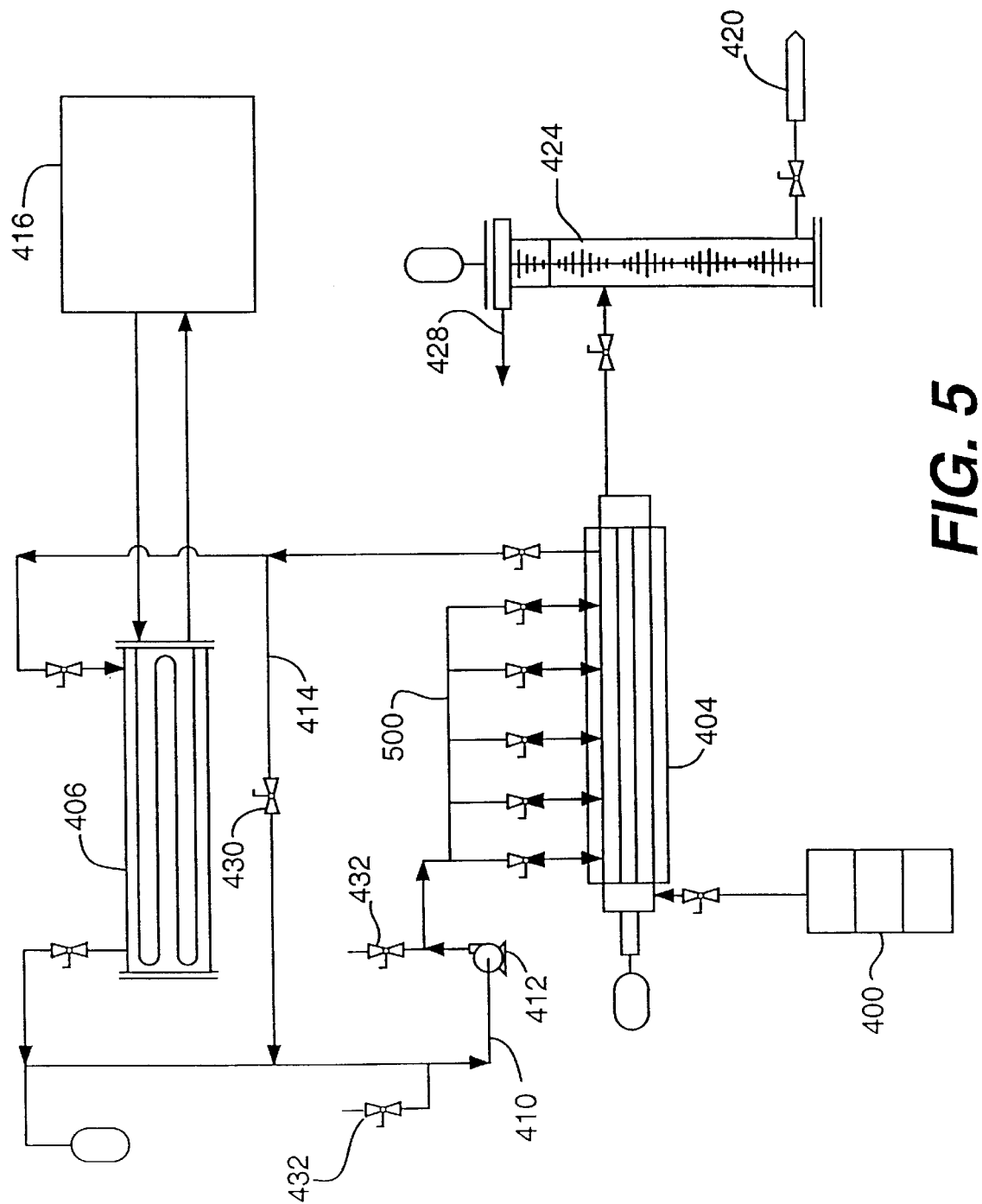
FIG. 5 is a schematic diagram illustrating a typical freeze concentration method of the invention employing a modified cooling system.

A typical freeze concentration method of the invention employing a modified cooling system is depicted in FIG. 5. As shown in FIG. 5, a modified cooling system 500 may be used in combination with a freeze concentration method of the invention to provide cooled refrigerant 410 at varying points along the axis of the crystallizer 404. By adding the cooled refrigerant at different points along the length of the crystallizer 404, a more even temperature distribution may be maintained throughout the length of the crystallizer 404. A representative example of a freeze concentration method of the invention wherein a portion of the recovered solid acid-rich phase is recycled back into the freeze concentration method is shown in schematic form in FIG. 6.

Figure 6:
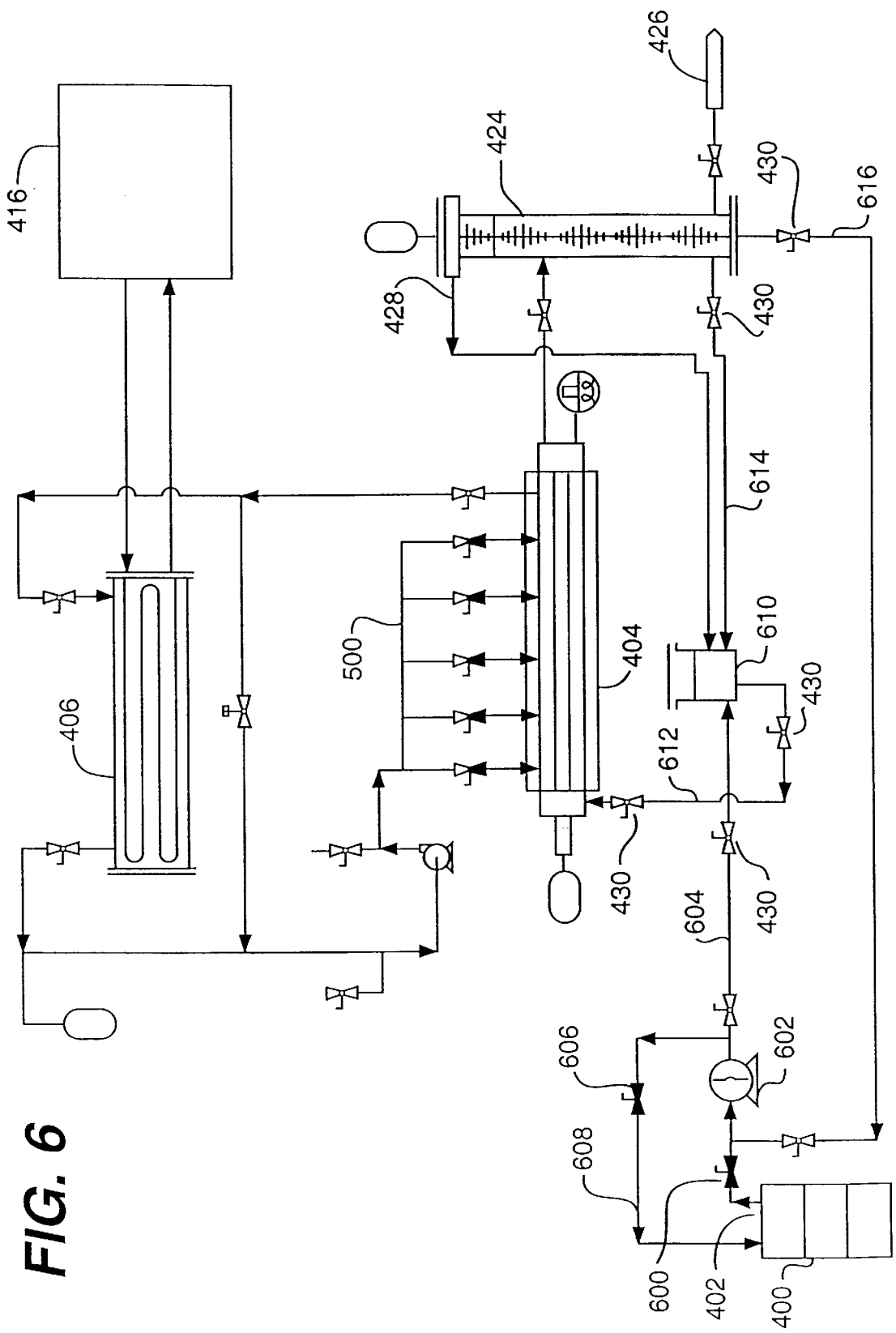
FIG. 6 is a schematic diagram illustrating a typical freeze concentration method of the invention wherein a portion of the recovered solid acid-rich phase is recycled back into the freeze concentration method.

As depicted in FIG. 6, a recirculation system may be employed in the freeze concentration method by mixing the initial feed stream 402 with a recycle stream 616 which contains a portion of the higher density product from the density column 424. Having mixed the initial feed stream 402 with the recycle stream 616, all or a portion of the mixed initial feed stream 604 may be pumped back to the feed source means of pump 602 via stream 608. The flow rates of the initial feed stream 604 and stream 608 may be controlled by valves 600 and 606. Additionally, the mixed initial feed stream 604 may be pumped into a feed tank 610 and combined with the components contained in recycle streams 428 and 614 which, respectively, recycle the low density and high density separated phase materials from density column 424. In the feed tank 610 the materials from the mixed initial feed stream 604 and recycle streams 428 and 614 may be combined to form a combined mixed material which is then fed to the crystallizer 404 via stream 612. By employing a feed tank 604 it is possible to maintain a full flooded system which reduces the number of pumps necessary for the processing of the aqueous waste stream. Indeed, the use of a feed tank 604 can provide a gravitational flooded system with improved control over the waste acid recovery process.

Figure 7:
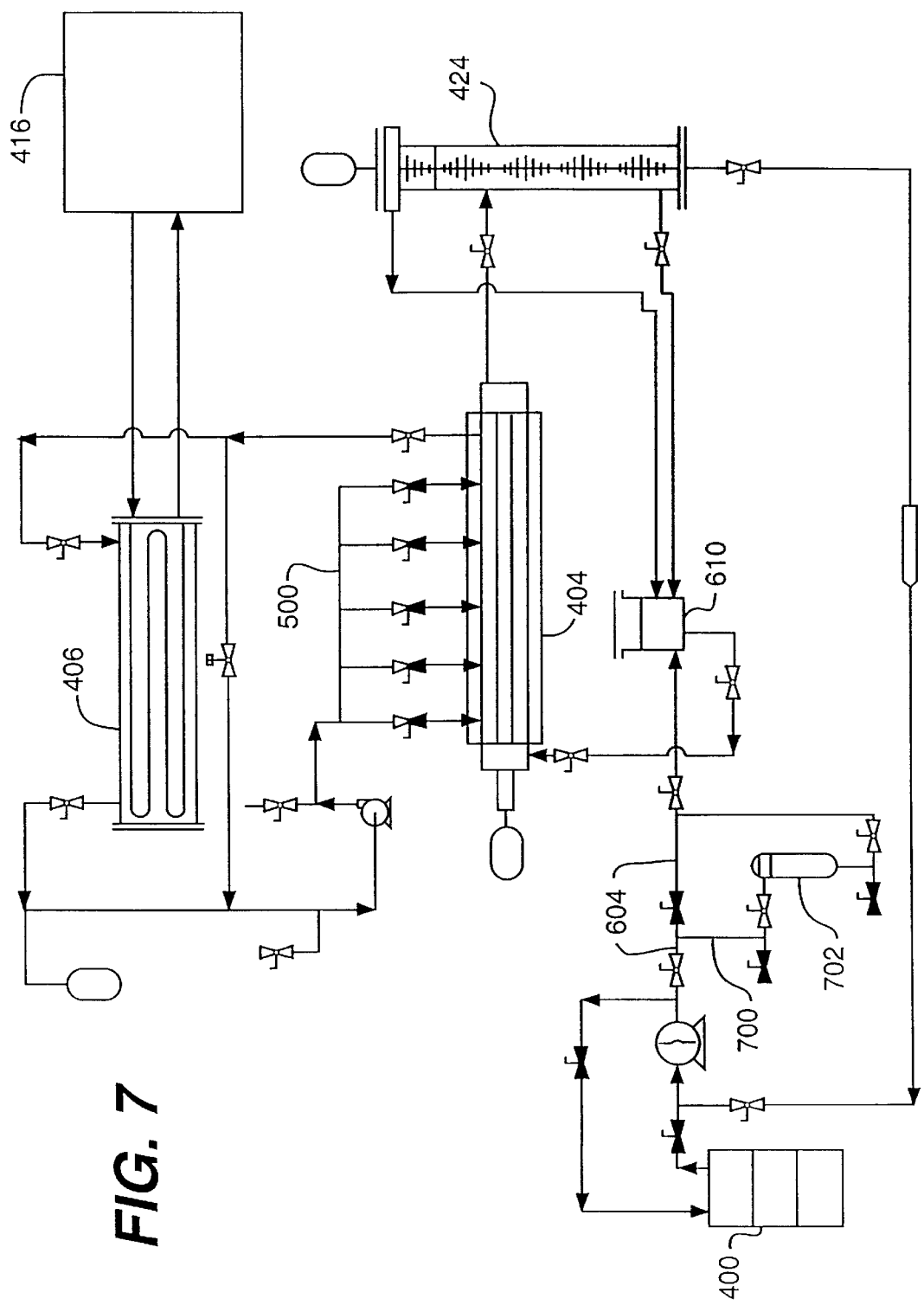
FIG. 7 is a schematic diagram illustrating a typical freeze concentration method of the invention employing a filter.

A filter may be employed in the freeze concentration method such as that depicted in FIG. 7. As shown in FIG. 7, all or a part of the mixed initial feed stream 604 may be conducted via stream 700 to a filter 702. Having filtered the mixed initial feed stream 604, the filtered stream 704 may be conducted to the feed tank 610. By filtering all or a portion of the mixed initial stream 604, it is possible to remove solid contaminants from the process. The removal of the solid contaminants can aid in prolonging the life of the crystallizer 404.

Figure 8:
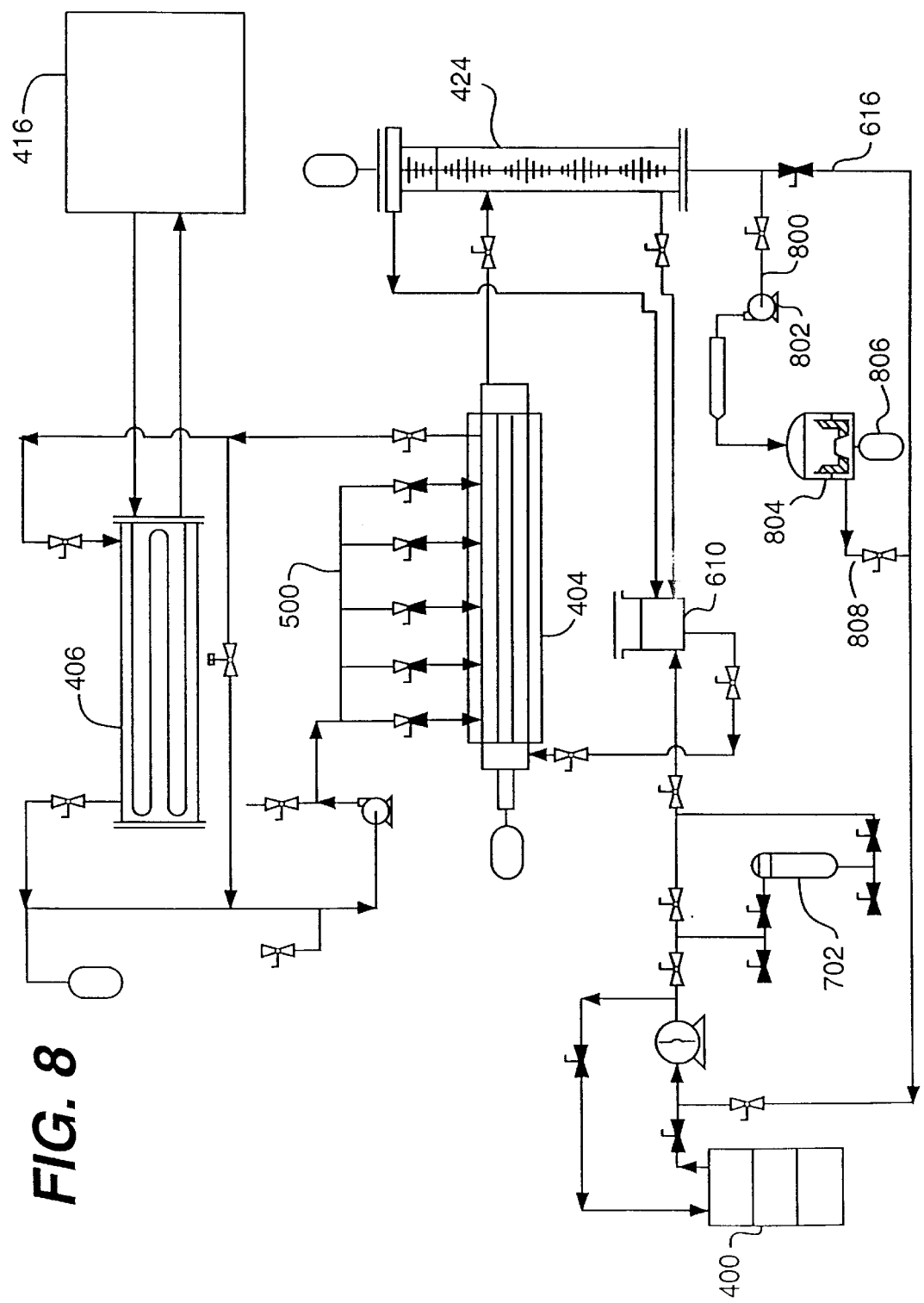
FIG. 8 is a schematic diagram illustrating a typical freeze concentration method of the invention employing a centrifuge in combination with density column.

In another embodiment of the invention, a centrifuge may be used in combination with a density column. An example of such a combination is depicted in FIG. 8. As shown in FIG. 8, all or a portion of the recycle stream 616 containing the higher density product from density column 424, may be pumped via stream 800 and pump 802 into a centrifuge 804 or caused to flow due to gravity via stream 800 into centrifuge 804. In the centrifuge 804 a mechanical force 806 is employed to centrifuge the higher density product such that an acid-rich region 806 is separated from an acid-poor region 808. The acid-rich region 806 is removed from the process and the acid-poor region 808 is conducted back via recycle stream 616 to the initial feed stream.

The sulfuric acid freeze concentration method of the invention may be used separately or in combination with other purification apparatus or processes. The method may be part of an industrial process to purify and recycle sulfuric acid solutions produced as a by-product of the process. Alternatively, the method may be used to purify and recycle aqueous sulfuric acid wastes as a stand alone process. Maximum benefits of the invention may be obtained when the method is practiced as a single pass process, using an apparatus such as that described and shown in FIG. 1 of U.S. Pat. No. 5,394,706.

The sulfric acid purification process may be classified as batch, continuous or semibatch. The purification process may also be carried out as a continuous, steady state process. In a preferred process, the incoming and outgoing solutions are allowed to flow continuously through the method. Such a continuous process preferably uses a sequential combination of a centrifuge and a density column or of a density column and a centrifuge. When the method of the invention is practiced as a continuous process, a portion of the denser, generally acid-rich stream or, alternatively, the lighter, generally acid-poor stream may be cycled back and combined with the initial aqueous sulfnric acid solution. The stream cycled back to and mixed with the initial aqueous sulfuric acid may be taken from the centrifuge, the density column, or both. Cycling back a portion of the acid-rich or acid-poor region allows the method to be operated within concentration ranges which form the solid and liquid phases of the slurry at a particular operating temperature. Mixing of the acid-rich or acid-poor stream with the initial aqueous sulfuric aid solution feed may be done before or after any precooling step.

EXAMPLES

A series of five test runs was conducted on organic waste products containing differing levels of sulfuric acid. In performing the tests, a feed organic waste stream was introduced into a freeze concentration apparatus, such as that depicted in FIG. 8. For the test runs a heat exchanger 406 cooled the refrigerant from an inlet temperature ranging from 10 to 20° F. to an outlet temperature of ranging from about 0 to 20° F. This cooled refrigerant was then pumped through a crystallizer 404 to provide a crystallizer inlet temperature ranging from about 0 to 20° F. and an outlet temperature ranging from about 5 to 30° F. By cooling crystallizer 404, the organic waste product stream passing through the crystallizer was cooled to an outlet temperature of about 45° F. The test runs were conducted over a period of about 4 hours.

In conducting the tests, the resulting solid sulfuric acid-rich phase was separated from the cooled organic waste stream. The sulfuric acid and total organic carbon weight percentages of the resulting solid sulfuric acid-rich phase were then measured. The results of these five test runs are provided in Tables 1 and 2 below:

TABLE 1

SULFURIC ACID (wt. %)

| Run Number | 1 | 2 | 3 | 4 | 5 |
|---|---|---|---|---|---|
| Feed Stream | 76.7 | 76.9 | 78.1 | 78.4 | 78.6 |
| Separated Acid-Rich Phase | 87.7 | 87.8 | 87.9 | 88.0 | 87.6 |

TABLE 2

TOTAL ORGANIC CARBON (wt. %)

| Run Number | 1 | 2 | 3 | 4 | 5 |
|---|---|---|---|---|---|
| Feed Stream | 6.7 | 6.7 | 6.7 | 7.4 | 7.4 |
| Separated Acid-Rich Phase | .27 | .26 | .23 | .23 | .11 |

As demonstrated in Tables 1 & 2, the separated acid-rich phase contained an average of about 10 wt % more sulfric acid than the initial feed stream while reducing the amount of total organic carbon by about 6.5 to about 7.3 wt %. Consequently, the total organic carbon was reduced by a factor ranging from about 30 to about 70. This enrichment of sulfuric acid demonstrates the ability of the freeze concentration method of the invention to produce industrial grade sulfuric acid from an organic waste product stream.

The claimed invention is:

1. A method of recovering a sulfuric acid from an aqueous waste stream containing sulfuric acid and an organic impurity comprising the steps of:

cooling the aqueous waste stream to a temperature at or near its freezing point to form a slurry of a solid sulfuric acid-rich phase and a liquid phase containing the organic impurity; and separating the sulfuric solid acid-rich phase and the liquid organic impurity phase on the basis of density;

wherein the slurry is formed in a scraped surface freeze crystallizer, the crystallizer comprising a surface onto which the solid phase forms and a scraper for removing the solid phase from the surface to form the slurry of the solid phase and the liquid phase, and wherein the crystallizer is cooled indirectly and is capable of controlling crystal growth in the crystallizer.

2. A method of claim 1, wherein the separation step comprises the steps of centrifuging the slurry to separate the solid sulfuric acid-rich phase and the liquid organic impurity phase.

3. A method of claim 1, wherein the sulfuric acid is present in an amount ranging from about 70 to about 90% by weight.

4. A method of claim 3, wherein the concentration of the sulfuric acid in the waste stream is enriched.

5. A method of claim 1, further comprising warming the separated solid sulfuric acid-rich phase to a temperature sufficient to melt the solid and form a liquid.

6. A method of recovering sulfuric acid from an aqueous waste stream containing sulfuric acid and an organic impurity comprising the steps of:

cooling an aqueous waste stream comprising an organic impurity and about 70 to about 90% by weight sulfuric acid to at or near its freezing point to form a mixture of a solid sulfuric acid-rich phase and a liquid organic phase in a scraped surface freeze crystallizer;

scraping the solid sulfuric acid-rich phase from the freeze crystallizer to form a solid-liquid slurry, the slurry having a solid sulfuric acid-rich phase and a liquid organic impurity phase;

removing the slurry from the freeze crystallizer; and separating the solid sulfuric acid-rich phase from the liquid organic impurity phase on the basis of density;

wherein the scraped surface freeze crystallizer is cooled indirectly and is capable of controlling crystal growth in the crystallizer.

7. A method of claim 6, further comprising warming the separated solid sulfuric acid-rich region to a temperature sufficient to melt the solid and form a liquid.

8. A method of claim 6, wherein the step of separating the solid sulfuric acid-rich region from the liquid organic waste region on the basis of density occurs in at least one of a density column or a centrifuge.

9. A method of claim 6, wherein the separation step comprises the steps of centrifuging the slurry to separate the solid sulfuric acid-rich phase and a liquid organic impurity phase.

10. A method of claim 6, further comprising warming the separated solid sulfuric acid-rich phase to a temperature sufficient to melt the solid and form a liquid.

11. A method of purifying an organic waste stream from an industrial process comprising the steps of:

cooling an organic waste stream comprising organic impurities, and sulfuric acid to a temperature at or near the freezing point of the organic waste stream to form a slurry of a solid sulfuric acid-rich phase and a liquid organic impurity phase;

separating the solid sulfuric acid-rich phase from the liquid organic impurity phase on the basis of density;

wherein the slurry is formed in a scraped surface freeze crystallizer, the crystallizer comprising a surface onto which the solid phase forms and a scraper for removing the solid phase from the surface to form the slurry of the solid phase and the liquid phase, and wherein the crystallizer is cooled indirectly and is capable of controlling crystal growth in the crystallizer.

12. A method of claim 11, wherein the step of separating the solid sulfuric acid-rich phase from the liquid organic impurity phase on the basis of density occurs in at least one of a density column or a centrifuge.

13. A method of claim 11, wherein the separated sulfuric acid-rich phase is recycled to the industrial process.

14. A method of claim 13, wherein the industrial process is a hydrocarbon alkylation process.

15. A method of claim 11, wherein the industrial process is a hydrocarbon alkylation process.

* * * * *